United States Patent [19]

Wade et al.

[11] 4,221,796
[45] Sep. 9, 1980

[54] SUBSTITUTED IMIDAZOLO-PYRIDINES AND METHOD

[75] Inventors: Peter C. Wade, Pennington; Jack Bernstein, New Brunswick; Rudiger D. Haugwitz, Titusville, all of N.J.

[73] Assignee: E. R. Squibb & Sons, Inc., Princeton, N.J.

[21] Appl. No.: 77,256

[22] Filed: Sep. 19, 1979

Related U.S. Application Data

[63] Continuation-in-part of Ser. No. 909,731, May 25, 1978, abandoned.

[51] Int. Cl.$^3$ .................... C07D 213/72; A61K 31/44
[52] U.S. Cl. ..................................... 424/256; 546/121
[58] Field of Search ......................... 546/121; 424/256

[56] References Cited

U.S. PATENT DOCUMENTS

| | | | |
|---|---|---|---|
| 3,701,780 | 10/1972 | Fisher | 546/121 |
| 4,092,321 | 5/1978 | Bochis | 546/121 |
| 4,096,264 | 6/1978 | Bochis et al. | 424/256 |
| 4,105,767 | 8/1978 | Bochis et al. | 424/256 |
| 4,146,642 | 3/1979 | Bochis et al. | 424/256 |
| 4,177,274 | 12/1979 | Bochis et al. | 424/256 |

Primary Examiner—Alan L. Rotman
Attorney, Agent, or Firm—Lawrence S. Levinson; Burton Rodney

[57] ABSTRACT

Imidazolo-pyridine derivatives are provided having the structure

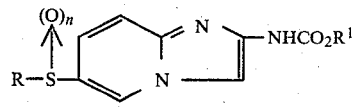

wherein R is lower alkyl, lower alkenylalkyl, lower alkynylalkyl, cycloalkyl, cycloalkenyl, cycloalkylalkyl, cycloalkenylalkyl or phenylalkyl and R$^1$ is lower alkyl, phenylalkyl or di-lower alkylaminoalkyl and n is 0, 1 or 2. These compounds are useful as anthelmintic agents administered orally or parenterally.

9 Claims, No Drawings

SUBSTITUTED IMIDAZOLO-PYRIDINES AND METHOD

REFERENCE TO OTHER APPLICATIONS

This application is a continuation-in-part of application Ser. No. 909,731, filed May 25, 1978, now abandoned.

DESCRIPTION OF THE INVENTION

The present invention relates to imidazolopyridine derivatives which are useful as anthelmintic agents and have the structure

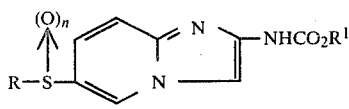
  I wherein R is lower alkyl, lower alkenylalkyl, lower alkynylalkyl, cycloalkyl, cycloalkenyl, cycloalkylalkyl, cycloalkenylalkyl or phenylalkyl and $R^1$ is lower alkyl, phenylalkyl or di-lower alkylaminoalkyl, and n is 0, 1 or 2.

The term "lower alkyl" or "alkyl" as used herein whether employed as an independent substituent or as a part of another substituent includes straight or branched chain aliphatic hydrocarbon radicals having up to and including 7 carbon atoms, preferably 1 to 3 carbons, such as methyl, ethyl, propyl, isopropyl, butyl, isobutyl, t-butyl, amyl, hexyl, heptyl and the like.

The term "lower alkenylalkyl" refers to an unsaturated hydrocarbon group having from 3 to 12 carbon atoms and a single carbon-carbon double bond in a position other than the α-position, that is, not adjacent to the sulfur atom. Typical lower alkenylalkyl groups include, for example, 2-propenyl, 2-butenyl, 3-butenyl, and the like.

The term "lower alkynylalkyl" refers to an unsaturated hydrocarbon group having from 3 to 12 carbon atoms, and a single carbon-carbon triple bond in a position other than the α-position, that is, not adjacent to the sulfur atom. Typical lower alkynylalkyl groups include, for example, 2-propynyl, 2-butynyl, 3-butynyl, and the like.

The term "phenylalkyl" as used herein refers to lower alkyl groups as discussed above having a phenyl substituent, such as benzyl.

The term "cycloalkyl" includes hydrocarbon groups containing 3 to 12 carbons, which include cyclopropyl, cyclobutyl, cyclopentyl, cyclohexyl, cycloheptyl, cyclooctyl, cyclodecyl and cyclododecyl, any of which groups may be substituted with 1, 2, 3 or 4 halogen and/or 1, 2, 3, or 4 lower alkyl groups.

The term "cycloalkenyl" includes cyclic hydrocarbon groups containing 3 to 10 carbons. Examples of suitable cycloalkenyl groups include cyclopropenyl, cyclobutenyl, cyclohexenyl, cycloheptenyl, cyclononeyl and cyclodecenyl, any of which groups may be substituted with 1 or 2 halogen and/or 1 or 2 lower alkyl groups. In the above cycloalkenyl rings, the double bond may be at any position in the ring.

The terms "cycloalkylalkyl" and "cycloalkenylalkyl" as used herein refers to cycloalkyl groups and cycloalkenyl groups as defined above linked to a lower alkyl group as defined above.

Where "alkyl" is employed as a linking group to the sulfur atom, such as in lower alkenylalkyl, lower alkynylalkyl, cycloalkylalkyl, cycloalkenylalkyl and the like, the "alkyl" group in such cases is a straight or branched chain "alkylene" group containing from 1 to 7 carbons in the normal chain, such as, for example,

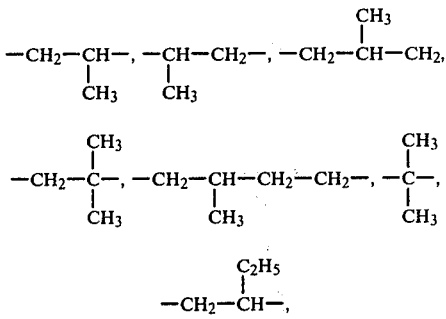

and the like.

Preferred are compounds of the invention wherein R is lower alkynylalkyl, cycloalkyl, cycloalkylalkyl, or cycloalkenylalkyl.

Most preferred compounds of the invention are those wherein n is 0 or 1, R is cycloalkyl, or cycloalkylalkyl, and $R^1$ is lower alkyl or phenylalkyl.

Thus, the compounds of the invention include the following:

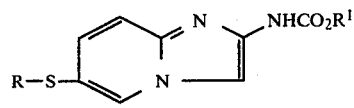
  II

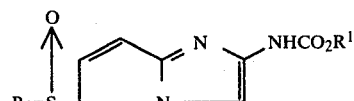
  III

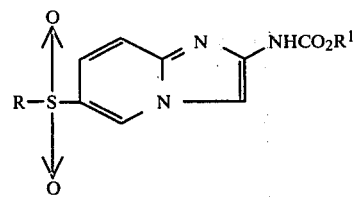
  IV

The compounds of the invention may be prepared according to the following reaction scheme:

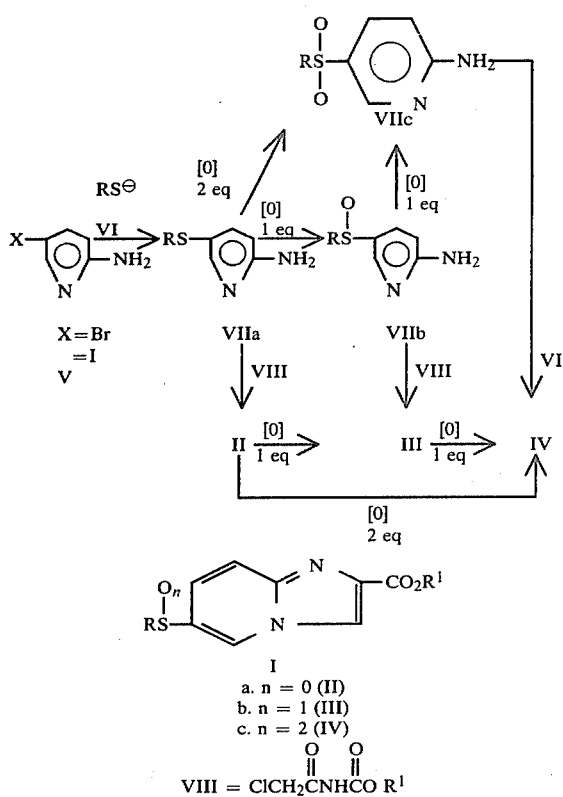

a. n = 0 (II)
b. n = 1 (III)
c. n = 2 (IV)

$$VIII = ClCH_2\overset{O}{\underset{\|}{C}}NH\overset{O}{\underset{\|}{C}}OR^1$$

The 2-amino-5-halopyridine (V) is prepared according to the method of Magidson and Menschikoff, Chem. Ber., 58, 115(1925); it is employed to prepare compounds of the invention of formula II as follows. The formula V compound is reacted with a suspension of an alkylthiol VI, copper powder as a catalyst, sodium methoxide in methanol with heating at a temperature within the range of from about 60° to about 200° C. for 1 to 24 hours to form the 2-amino-5-alkylthiopyridine of formula VIIa.

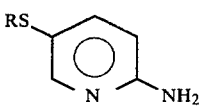

VIIa

Alternatively, the formula VIIa compound may be prepared by heating a suspension of potassium alkylthiolate and the 2-amino-5-halopyridine in 1-methyl-2-pyrrolidinone under an inert atmosphere such as nitrogen for periods of 1 to 12 hours.

The formula VIIa compound is then reacted with the chloroacetylcarbamate VIII

VIII in hexamethylphosphoric triamide (HMPT) or other non-reacting solvents at temperatures within the range of from about 50° to about 200° C. for periods ranging from 1 to 8 hours to form the formula II thio compound of the invention.

The formula III sulfinyl compound of the invention may be prepared by oxidizing the 2-amino-5-(alkylthio)-pyridine VIIa employing an oxidizing agent such as one equivalent of peracetic acid or m-chloroperbenzoic acid to form the 2-amino-5-(alkylsulfinyl)pyridine VIIb

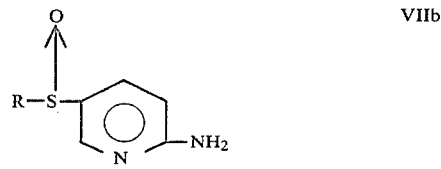

VIIb which is then reacted with the chloroacetylcarbamate VIII as described above to form the formula III sulfinyl compound of the invention.

The formula IV sulfonyl compound of the invention may be prepared by oxidizing the 2-amino-5-(alkylthio)-pyridine VIIa with 2 equivalents of m-chloroperbenzoic acid or oxidizing the 2-amino-5-(alkylsulfinyl)pyridine VIIb with one equivalent of m-chloroperbenzoic acid to form the 2-amino-5-(alkylsulfonyl)pyridine VIIc

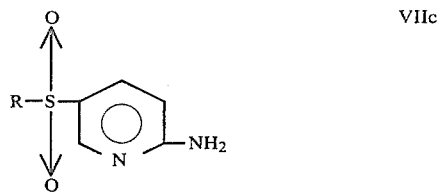

VIIc which is then reacted with the chloroacetylcarbamate VIII as described above to form the formula IV sulfonyl compound of the invention.

Alternatively, the sulfinyl compounds of formula III may be prepared by oxidizing thio compounds of formula II utilizing one equivalent of an oxidizing agent such as m-chloroperbenzoic acid, sodium m-periodate or hydrogen peroxide in acetic acid. Additional routes are outlined in Houben-Weyl's *Methoden Der Organischen Chemie*, Vol. 9, pp. 211-217 (1955), C. Thieme Verlag, Stuttgart.

The sulfonyl compounds of formula IV may be prepared by oxidizing thio compounds of formula II utilizing two equivalents of an oxidizing agent as described above or by oxidizing sulfinyl compounds of formula III utilizing one equivalent of such oxidizing agent.

Various starting materials employed in the above reactions are either known in the art or easily prepared according to conventional techniques.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with a nontoxic, edible carrier to form a feed supplement, or may be administered in unit dosage forms such as powders, capsule, tablet, boluses, drenches, etc.

Where the compounds are administered parenterally, they may be dispersed (for example, suspended) in nontoxic non-pyrogenic physiologically acceptable carriers such as water, benzyl benzoate, 1,3-butylene glycol, ethyl oleate, glyceryl triacetate, castor oil, sesame oil, and sesame oil:benzyl benzoate (1:1). The parenteral product will usually take the form of a suspension containing from about 1 to about 10% by weight of the compound of formula I in anyone or mixture of the above carriers.

In general, the compounds of formula I exhibit anthelmintic activity when administered to animals (parenterally or orally) in a single dose of about 1 to about 100 mg per kilogram of animal body weight. It is preferred to employ in the range of 2.5–25 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

6-(Methylthio)imidazo[1,2-a]pyridine-2-carbamic acid, methyl ester

A. 2-Amino-5-iodopyridine

Iodination of 2-aminopyridine is accomplished in 60% yield according to the method of Magidson and Menschikoff, m.p. 126°–128° C., after recrystallization from benzene.

B. 2-Amino-5-(methylthio)pyridine

A suspension of Cu powder (9.0 g), NaOMe (34.5 g, 0.638 mol), methylthiol (0.642 mol), and 2-amino-5-iodopyridine (100 g, 0.455 mol) in 800 ml of MeOH is heated in an autoclave at 150° C. for 12 hours. After cooling, the reaction mixture is filtered, and the filtrate is evaporated in vacuo. The residue is partitioned between EtOAc and $H_2O$. The organic layer is separated, washed with $H_2O$, dried and evaporated in vacuo. Recrystallization from MeOH yields the title compound.

C. Methyl(chloroacetyl)carbamate

A suspension of 2-chloroacetamide (122.6 g, 1.31 mol) in 300 ml of 1,2-dichloroethane is cooled to 0° C. and treated with oxalyl chloride (200 g, 1.57 mol). The reaction mixture is heated at reflux for 4 hours. After cooling to 5° C., 68 ml of MeOH is added dropwise while keeping the internal temperature below 15° C. with external cooling. After addition is complete, the product is separated by filtration and washed with $CH_2Cl_2$ and $Et_2O$. Recrystallization from $CH_2Cl_2$ yields methyl(chloroacetyl)carbamate.

D. 6-(Methylthio)imidazo[1,2-a]pyridine-2-carbamic acid, methyl ester

A suspension of 2-amino-5-(methylthio)pyridine (0.667 mol) and methyl(chloroacetyl)carbamate (0.667 mol) in 325 ml of HMPT is heated at 100° C. for 5 hours. After dilution with 2000 ml of $H_2O$, the product is collected by filtration, successively washed with $H_2O$, MeOH and $CH_2Cl_2$, and dried.

EXAMPLE 2

6-(Methylsulfinyl)imidazo[1,2-a]pyridine-2-carbamic acid, methyl ester

A. 2-Amino-5-(methylsulfinyl)pyridine

A solution of 2-amino-5-(methylthio)pyridine (10.1 g, 50 mmol) and 200 ml of $CH_2Cl_2$ is treated dropwise with 200 ml of $CH_2Cl_2$ containing 85% m-chloroperbenzoic acid (10.15 g, 50 mmol) at 20° C. After the addition is complete, the reaction mixture is stirred an additional 15 minutes and washed with 500 ml of saturated $NaHCO_3$ solution. The organic layer is separated, washed with $H_2O$, and dried. Evaporation of the solvent in vacuo and recrystallization from EtOH yields the title compound.

B. 6-(Methylsulfinyl)imidazo[1,2-a]pyridine-2-carbamic acid, methyl ester

A suspension of 2-amino-5-(methylsulfinyl)pyridine (7.9 mmol) and methyl(chloroacetyl)carbamate (11.6 mmol) in 12 ml of HMPT is treated in a manner similar to that described in Example 1D to yield the product.

EXAMPLE 3

6-(Methylsulfonyl)imidazo[1,2-a]pyridine-2-carbamic acid, methyl ester

A. 2-Amino-5-(methylsulfonyl)pyridine

The reaction of 74.6 mmol of 2-amino-5-(methylthio)-pyridine with 31.8 g (156 mmol) of m-chloroperbenzoic acid carried out in a manner similar to that described with respect to Example 2A yields, after recrystallization from EtOH, the title A compound.

B. 6-(Methylsulfonyl)imidazo[1,2-a]pyridine-2-carbamic acid, methyl ester

A suspension of 2-amino-5-(methylsulfonyl)pyridine (58.7 mmol) and methyl(chloroacetyl)carbamate (70 mmol) in 88 ml of HMPT is treated in a manner similar to that described above with respect to Example 1D to yield the product.

EXAMPLE 4

6-(Methylsulfinyl)imidazo[1,2-a]pyridine-2-carbamic acid, methyl ester

A suspension of 6-(methylthio)imidazo[1,2-a]pyridine-2-carbamic acid, methyl ester (prepared as described in Example 1) (0.447 mol) in 2700 ml of HOAc is treated dropwise with 535 ml of 30% $H_2O_2$. The suspension is stirred until a solution is obtained (~5 hours) and then poured into 8 l. of ice water. The product is collected by filtration and dried.

EXAMPLE 5

6-(Methylsulfonyl)imidazo[1,2-a]pyridine-2-carbamic acid, methyl ester 6-(Methylthio)imidazo[1,2-a]pyridine-2-carbamic acid, methyl ester (prepared as described in Example 1) (0.00159 mol) is added to a solution of trifluoroperacetic acid prepared from 415 μl of trifluoroacetic anhydride with 65 μl of 90% $H_2O_2$ in 5 ml of $CH_2Cl_2$. The solution is refluxed for 90 minutes. After washing the solution with saturated aqueous $NaHCO_3$, the solvent is removed in vacuo. The residue is chromatographed over 50 g of silica gel and eluted with 50% $EtOAc$—$CH_2Cl_2$ to yield the title compound.

EXAMPLES 6 TO 21

Following the procedure of Example 1 but substituting for methylthiol, the thiol derivative shown in Column I of Table I set out below, and substituting for methyl(chloroacetyl)carbamate, the compound shown in Column II, the product in accordance with the present invention shown in Column III is obtained.

TABLE I

| Ex. No. | Column I (RS⁻) R | Column II (ClCH₂CNHCOR¹) R¹ | Column III R | Column III R¹ |
|---|---|---|---|---|
| 6. | i-C₃H₇ | C₂H₅ | as in Column I | as in Column II |
| 7. | ▷—CH₂ | C₆H₅CH₂ | | |
| 8. | CH₂=CH—CH₂ | CH₃ | | |
| 9. | (CH₃)₂CHCH₂ | C₃H₇ | | |
| 10. | CH≡C—CH₂ | (CH₃)₂NCH₂CH₂ | | |
| 11. | Cl₂C(CH₂)— (dichlorocyclopropylmethyl) | C₆H₅CH₂ | | |
| 12. | cyclobutyl | CH₃ | | |
| 13. | C₆H₅CH₂ | C₆H₅CH₂ | | |
| 14. | Cl₂C(CH₃)(CH₂)— | (CH₃)₂N(CH₂)₂ | | |
| 15. | cyclobutyl | CH₃ | | |
| 16. | (CH₃)₂CHCH₂ | CH₃ | | |
| 17. | cyclopropylmethyl | C₆H₅CH₂ | | |
| 18. | CH₂=CHCH₂ | C₆H₅CH₂ | | |
| 19. | cyclobutylmethyl | (C₂H₅)₂N—CH₂CH₂ | | |
| 20. | Cl₂C(CH₂)— | C₆H₅CH₂ | | |
| 21. | CH₂=CH—CH₂ | CH₃ | | |

EXAMPLES 22 TO 37

Following the procedure of Example 4 except substituting the compounds of Examples 6 to 21 for the 6-(methylthio)imidazo[1,2-a]pyridine-2-carbamic acid, methyl ester as shown in Column I of Table II set out below, the corresponding sulfides of the compounds of Examples 6 to 21 as set out in Column II are obtained.

EXAMPLES 38 TO 53

Following the procedure of Example 5 but substituting the compounds of Examples 6 to 21 for 6-(methylthio)imidazo[1,2-a]pyridine-2-carbamic acid, methyl ester as shown in Column I of Table III set out below, the corresponding sulfoxides shown in Column II are obtained.

TABLE II

| | Column I | | Column II | |
|---|---|---|---|---|
| Ex. No. | R | $R^1$ | R | $R^1$ |
| 22. | i-$C_3H_7$ | $C_2H_5$ | as in Column I | |
| 23. | ▷—$CH_2$ | $C_6H_5CH_2$ | | |
| 24. | $CH_2$=CH—$CH_2$ | $CH_3$ | | |
| 25. | $(CH_3)_2CHCH_2$ | $C_3H_7$ | | |
| 26. | CH≡C—$CH_2$ | $(CH_3)_2NCH_2CH_2$ | | |
| 27. | Cl,Cl-cyclopropyl-$CH_2$ | $C_6H_5CH_2$ | | |
| 28. | cyclobutyl | $CH_3$ | | |
| 29. | $C_6H_5CH_2$ | $C_6H_5CH_2$ | | |
| 30. | Cl,Cl-cyclopropyl($CH_3$)-$CH_2$ | $(CH_3)_2N(CH_2)_2$ | | |
| 31. | cyclobutyl | $CH_3$ | | |
| 32. | $(CH_3)_2CHCH_2$ | $CH_3$ | | |
| 33. | cyclopropyl-$CH_2$ | $C_6H_5CH_2$ | | |
| 34. | $CH_2$=CHCH$_2$ | $C_6H_5CH_2$ | | |
| 35. | cyclobutyl-$CH_2$ | $(C_2H_5)_2N$—$CH_2CH_2$ | | |
| 36. | Cl,Cl-cyclopropyl-$CH_2$ | $C_6H_5CH_2$ | | |
| 37. | $CH_2$=CH—$CH_2$ | $CH_3$ | | |

TABLE III

| | Column I | | Column II | |
|---|---|---|---|---|
| Ex. No. | R | $R^1$ | R | $R^1$ |
| 38. | i-$C_3H_7$ | $C_2H_5$ | as in Column I | |
| 39. | ▷—$CH_2$ | $C_6H_5CH_2$ | | |

TABLE III-continued

| | Column I | | Column II | |
|---|---|---|---|---|
| Ex. No. | R | R¹ | R | R¹ |
| 40. | CH$_2$=CH—CH$_2$ | CH$_3$ | | |
| 41. | (CH$_3$)$_2$CHCH$_2$ | C$_3$H$_7$ | | |
| 42. | CH≡C—CH$_2$ | (CH$_3$)$_2$NCH$_2$CH$_2$ | | |
| 43. | Cl$_2$C(cyclopropyl)CH$_2$ | C$_6$H$_5$CH$_2$ | | |
| 44. | cyclobutyl-CH$_2$ (implied) | CH$_3$ | | |
| 45. | C$_6$H$_5$CH$_2$ | C$_6$H$_5$CH$_2$ | | |
| 46. | Cl$_2$C(cyclopropyl, CH$_3$)CH$_2$ | (CH$_3$)$_2$N(CH$_2$)$_2$ | | |
| 47. | cyclobutyl | CH$_3$ | | |
| 48. | (CH$_3$)$_2$CHCH$_2$ | CH$_3$ | | |
| 49. | cyclopropyl-CH$_2$ | C$_6$H$_5$CH$_2$ | | |
| 50. | CH$_2$=CHCH$_2$ | C$_6$H$_5$CH$_2$ | | |
| 51. | cyclobutyl-CH$_2$ | (C$_2$H$_5$)$_2$N—CH$_2$CH$_2$ | | |
| 52. | Cl$_2$C(cyclopropyl)CH$_2$ | C$_6$H$_5$CH$_2$ | | |
| 53. | CH$_2$=CH—CH$_2$ | CH$_3$ | | |

What is claimed is:

1. A compound of the structure

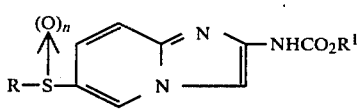

wherein R is lower alkynylalkyl containing 3 to 12 carbons, cycloalkyl containing 3 to 12 carbons, cycloalkenyl containing 3 to 10 carbons, cycloalkylalkyl containing 3 to 12 carbons in the cycloalkyl portion and up to 7 carbons in the alkyl portion, or cycloalkenylalkyl containing 3 to 10 carbons in the cycloalkenyl portion and up to 7 carbons in the alkyl portion and R¹ is lower alkyl, phenylalkyl containing up to 7 carbons in the alkyl portion or di-lower alkylaminoalkyl containing up to 7 carbons in the alkyl portion and n is 0, 1 or 2, and physiologically acceptable salts thereof.

2. The compound as defined in claim 1 wherein n is 0.

3. The compound as defined in claim 1 wherein n is 1.

4. The compound as defined in claim 1 wherein R¹ is lower alkyl and n is 0 or 1.

5. The compound as defined in claim 1 wherein R is cycloalkylalkyl, R¹ is lower alkyl and n is 0 or 1.

6. An anthelmintic composition comprising an effective amount of a compound as defined in claim 1 mixed with a pharmaceutically acceptable carrier therefor.

7. A method for treating or preventing helminth infestation in mammalian hosts which comprises administering to a mammal an effective amount of an anthelmintic composition as defined in claim 6.

8. The method as defined in claim 7 wherein said composition is administered orally or parenterally.

9. The method as defined in claim 7 wherein said composition is administered parenterally.

* * * * *